(12) United States Patent
Colin et al.

(10) Patent No.: US 9,952,593 B2
(45) Date of Patent: Apr. 24, 2018

(54) COLLABORATIVE ROBOT FOR VISUALLY INSPECTING AN AIRCRAFT

(71) Applicant: AIRBUS GROUP SAS, Blagnac (FR)

(72) Inventors: Nicolas Colin, Toulouse (FR); Frank Guibert, Toulouse (FR)

(73) Assignee: AIRBUS, Blagnac (FR)

( * ) Notice: Subject to any disclaimer, the term of this patent is extended or adjusted under 35 U.S.C. 154(b) by 0 days.

(21) Appl. No.: 15/030,845

(22) PCT Filed: Oct. 23, 2014

(86) PCT No.: PCT/EP2014/072785
§ 371 (c)(1),
(2) Date: Apr. 20, 2016

(87) PCT Pub. No.: WO2015/059241
PCT Pub. Date: Apr. 30, 2015

(65) Prior Publication Data
US 2016/0264262 A1    Sep. 15, 2016

(30) Foreign Application Priority Data
Oct. 24, 2013  (FR) ..................................... 13 60395

(51) Int. Cl.
*G05B 19/18*       (2006.01)
*G05D 1/00*        (2006.01)
(Continued)

(52) U.S. Cl.
CPC ............ *G05D 1/0038* (2013.01); *B25J 5/007* (2013.01); *B25J 19/023* (2013.01); *B64F 5/60* (2017.01);
(Continued)

(58) Field of Classification Search
CPC .......... G05D 1/0038; B64F 5/60; B25J 5/007; B25J 19/023; G01N 29/04; G01N 29/226
See application file for complete search history.

(56) References Cited

U.S. PATENT DOCUMENTS

2003/0089183 A1*  5/2003  Jacobsen .............. G01N 29/045
                                                          73/865.8
2010/0235037 A1*  9/2010  Vian ...................... G07C 5/008
                                                          701/31.4
(Continued)

FOREIGN PATENT DOCUMENTS

DE   10 2009 015648 A1   12/2010
WO   2012/047479 A1   4/2012
WO   2012/050803 A2   4/2012

*Primary Examiner* — Ian Jen
(74) *Attorney, Agent, or Firm* — Im IP Law; C. Andrew Im

(57) ABSTRACT

A device for visually inspecting the external surfaces of an aircraft includes an inspection area to receive an aircraft, at least one visual inspection robot, and a control center. A movable platform of the robot supports a turret having an observation unit. The robot includes a processing unit which guides the movable platform and process the data received from the observation unit. The processing unit of the robot are configured to autonomously control the robot during the visual inspection of the external surfaces of the aircraft parked in the inspection area; to interrupt a visual inspection in the event of a detection of an anomaly on the external surface of the aircraft; to transmit a visual inspection data to the control center; and to receive instructions from the control center.

22 Claims, 3 Drawing Sheets

(51) Int. Cl.
 *B25J 5/00* (2006.01)
 *B25J 19/02* (2006.01)
 *B64F 5/60* (2017.01)
 *G01N 29/04* (2006.01)
 *G01N 29/22* (2006.01)

(52) U.S. Cl.
 CPC ............ *G01N 29/04* (2013.01); *G01N 29/226* (2013.01); *G01N 2291/2694* (2013.01); *G05B 2219/45066* (2013.01); *G05D 2201/0207* (2013.01); *Y10S 901/44* (2013.01)

(56) References Cited

U.S. PATENT DOCUMENTS

2012/0081540 A1* 4/2012 Jang .................. B64F 5/0045
 348/128
2013/0261876 A1* 10/2013 Froom ................ B64F 5/0045
 701/29.3

\* cited by examiner

COLLABORATIVE ROBOT FOR VISUALLY INSPECTING AN AIRCRAFT

RELATED APPLICATIONS

This application is a § 371 application from PCT/EP2014/072785 filed Oct. 23, 2014, which claims priority from French Patent Application No. 13 60395 filed Oct. 24, 2013, each of which is incorporated herein by reference in its entirety.

FIELD OF THE INVENTION

The present invention belongs to the field of the non-destructive testing of aircraft.

More particularly, the invention relates to a collaborative robot for visually inspecting an aircraft on the ground as part of the inspection or test operations and relates to an inspection method employing such a robot. The invention in particular finds an application in the field of pre-flight checks on an aircraft.

BACKGROUND OF THE INVENTION

In the field of aircraft, visual inspections, pre-flight or during maintenance operations, form part of the periodic checks that ensure the operational safety of the aircraft.

Specifically, visual inspection makes it possible to detect anomalies that may arise in visible parts of the aircraft which are often those parts that are most exposed to external influences and, in some instances, may reveal deeper damage to the structure.

Furthermore, visual inspection does not require any particular dismantling, at the very most requiring the opening of doors or inspection hatches, which means that the inspection can be carried out relatively rapidly.

Historically, and still in widespread use even now, visual inspection has been performed by an operator on the ground, this operator for example being a technician or a pilot of the aircraft.

Inspection by an operator on the ground is performed in accordance with a check list, but the operator is free to inspect other elements or zones of the aircraft than those listed on the check list, particularly if indications lead him to take an interest in a particular zone, thereby making it possible to improve the detection of any potential anomalies.

On the other hand, an operator may be more or less attentive and may become distracted by observations that are not necessarily the most significant observations, at the risk of neglecting certain detailed information that ought to give him cause to make a more in-depth examination and perform an analysis.

In order to avoid the unpredictability of human intervention, it has been considered for visual inspections to be carried out automatically. For that, systems employing video cameras that are fixed with respect to the ground, for example in a hangar, or that are mobile and carried by robots moving over the ground or in flight, have been conceived of. Patent application WO2012/047479 illustrates one example of an automated airplane inspection device. The inspection of the airplane is assigned to a set of cameras that are fixed or able to move along the ground by means of rolling robots or able to move in flight by means of flying robots which are assigned to various parts of the airplane. The viewing means communicate with a remote computer center which processes the images received in order therefrom to deduce the presence of anomalies and determine what maintenance operations are to be carried out.

In such a system, the image processing and image interpretation are performed automatically which means that the checking operations can be performed without human intervention, the decision-making being assigned to the automatic system. While the unpredictabilities of a human operator are thus avoided, what is then lost is the benefit of the observation made by the operator who has a large capacity for interpretation, particularly when faced with new and uninventoried situations that may prove difficult to interpret. Furthermore, a device that carries out automatically tests that touch on matters of safety presents potential problems with certification because of the need to demonstrate the high degree of reliability of the system.

OBJECT AND SUMMARY OF THE INVENTION

In order to avoid the difficulties of the known solutions, the device of the invention for the visual inspection of the exterior surfaces of an aircraft comprises an inspection area intended to accept an aircraft and comprises at least a visual inspection robot of which a mobile platform carries a turret with viewing means and comprises processing means that guide the mobile platform and process information received from the viewing means. Furthermore, the visual inspection device comprises a control center with a station for at least one control operator, and the processing means of the visual inspection robot are designed to:

drive the visual inspection robot autonomously during a visual inspection of the exterior surfaces of an aircraft parked on the inspection area;

interrupt an on-going visual inspection in the event of an anomaly being detected on the exterior surface of an aircraft during the course of inspection;

transmit visual inspection information to the control center;

receive instructions from the control center as to what follow-up action to perform after a visual inspection.

This then yields a device for the visual inspection of an aircraft that is entirely controlled by a remote operator assisted by a collaborative robot that performs the visual inspection tasks near the aircraft.

Advantageously, the visual inspection robot comprises means for determining at any time during the course of an inspection the position of the visual inspection robot and the orientation of the viewing means in an axis system connected with the aircraft.

The robot is thus able to move autonomously with respect to the airplane both for managing the movements thereof and for managing which zones of the aircraft are to undergo visual inspection.

In one embodiment, the processing means of the robot are designed to determine the position of the robot and the orientation of the viewing means by processing images of the aircraft being inspected and that are obtained by the viewing means.

Such a means allows the position of the robot with respect to the airplane to be reset even if the airplane does not have an exact position with respect to the theoretical position it ought to have and allows deviations from this position to be corrected without measurements or means external to the device.

In one embodiment, the visual inspection robot comprises absolute-location means, such as GPS receiver or laser telemeters aimed at reference targets, or means of integrating its movements, for example by odometry.

The robot is thus capable of moving independently of any resetting with respect to the position of the aircraft in order to move in close to the aircraft and after resetting determine its precise position during its own actual movements without establishing its position continuously by direct observation of the aircraft.

Furthermore, the visual inspection device comprises all or some of the following features:

The processing means comprise data storage means storing data comprising, at least temporarily, characteristics, particularly geometric and graphic characteristics, of an aircraft being inspected. The robot thus locally has access to nominal characteristics of the aircraft that it is to inspect and with respect to which it is to visually identify any potential anomalies.

The processing means comprise data storage means storing data comprising anomaly characteristics, for example in an anomalies library. The robot, in addition to having logic engines for identifying anomalies that are not necessarily inventoried, is thus capable of comparing any visual element observed with known anomalies.

The processing means comprise image processing algorithms for detecting, in images transmitted by the viewing means, anomalies visible in at least one of the wavelengths belonging to the optical spectrum.

The viewing means comprise illuminating means illuminating with light from the visible domain or from the infrared domain or from the ultraviolet domain.

Thus, not only are zones of the aircraft that may be naturally weakly illuminated illuminated, but also, anomalies sensitive to certain light spectra or for which the visual contrast is increased at certain wavelengths of the light spectrum are revealed.

The viewing means and the processing means are configured to determine a three-dimensional shape of the inspected exterior surfaces of the aircraft. It is thus possible to identify what shapes of the exterior surface of the aircraft do not conform to the nominal shapes.

In one embodiment of the device, the visual inspection device comprises means for the non-destructive testing of the structure of the inspected aircraft.

The non-destructive testing means are carried by the visual inspection robot or are carried, in full or in part, by at least one control robot the behavior of which is controlled by the visual inspection robot.

It is thus possible to confirm or negate the fact that the visual anomaly is an indication of a deeper structural anomaly and to measure non-visible damage.

The viewing means are orientable in elevation and in azimuth with respect to a frame of reference of the platform of the visual inspection robot. It is thus possible quickly to scan all the exterior surfaces of the aircraft which are visible to the robot as it moves.

In one embodiment, the processing means are configured to determine the position of a defect detected on an aircraft with respect to elements of the internal structure of said aircraft which are not visible from the outside of the aircraft. The consequences of the defect are thus better evaluated and the position of the defect is located for the maintenance operators with respect to identifiable concrete structural elements.

For example the inspection robot is a robot traveling by rolling over the ground of the inspection area or by hovering in a volume the footprint of which corresponds substantially to the inspection area.

In one embodiment of the device, use is made of a plurality of inspection robots configured to carry out a visual inspection of one and the same aircraft jointly. A visual inspection can thus be carried out more rapidly and, if appropriate, more fully if specialist robots are used for inspecting certain zones.

The invention also relates to a visual inspection method for the visual inspection of an aircraft in which method images of an exterior surface of the aircraft being inspected are transmitted to processing means of a visual inspection robot, in which the processing means analyze the images in order to identify the presence of any potential visible anomalies, and in which when a visible anomaly is detected, the data relating to the detected anomaly are transmitted to a control center and the visual inspection is interrupted, at least when the processing means identify an anomaly belonging to a category of anomalies considered to be critical.

Advantageously, when the inspection is interrupted because an anomaly has been detected, instructions are transmitted to the visual inspection robot by the control center to continue with the visual inspection, said instructions determining how the robot is to continue the inspection.

In one embodiment, the amplitude of a visible anomaly is calculated by the processing means using optical means of measuring deformations and/or by colorimetric analysis in the visible and/or infrared and/or ultraviolet domain of the light spectrum.

In one embodiment, when an anomaly is visually detected, a zone affected by the visible anomaly is subjected to non-destructive testing by the visual inspection robot or by a non-destructive testing robot controlled by the visual inspection robot.

BRIEF DESCRIPTION OF THE DRAWINGS

The invention is described with reference to the figures which schematically depict one nonlimiting embodiment of the invention.

DETAILED DESCRIPTION OF THE EMBODIMENTS

Figure 1:
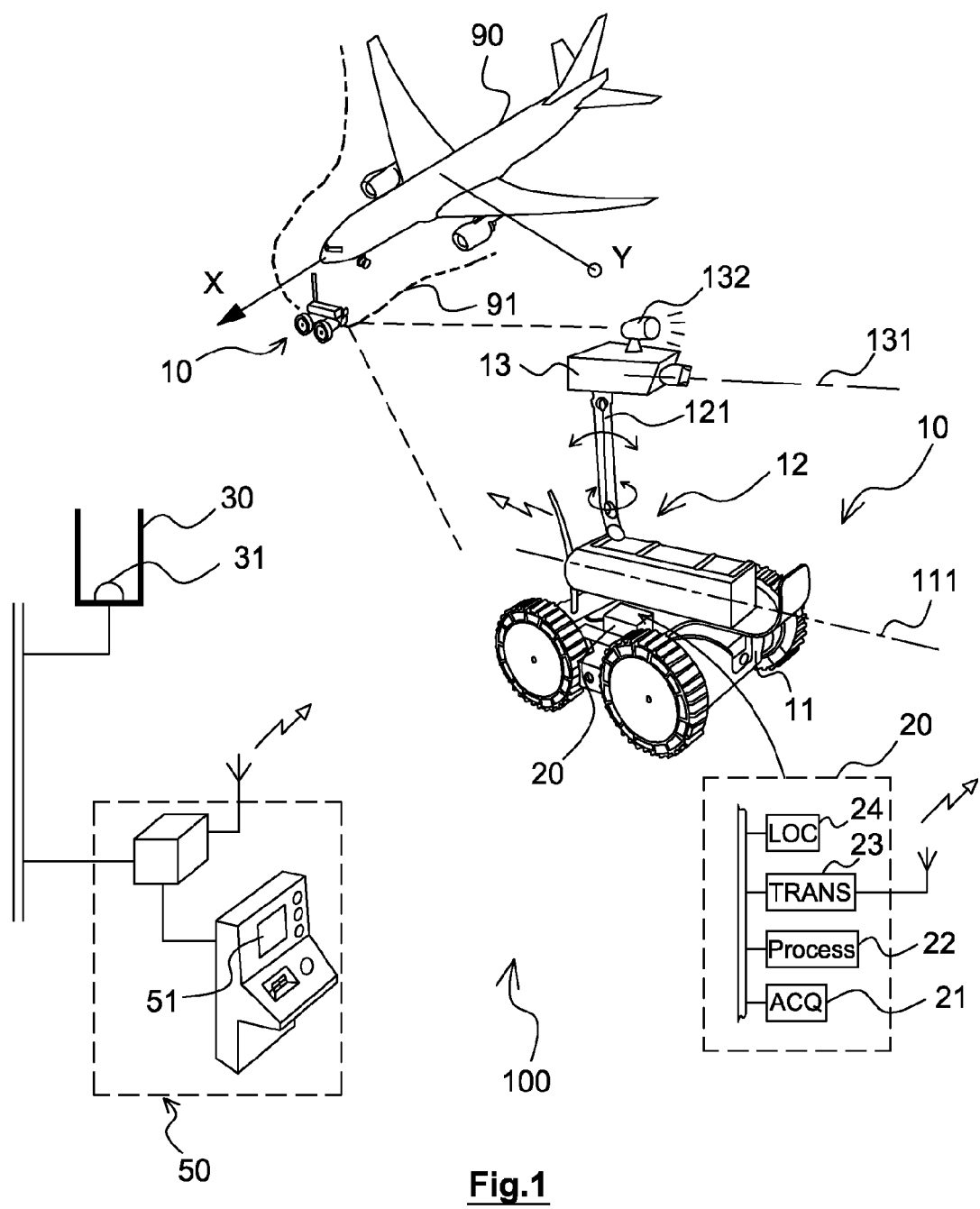
FIG. 1 is an example of an overall layout of the main components of a device for the visual inspection of an aircraft implementing a collaborative robot and a remote control center.
Figure 2A:
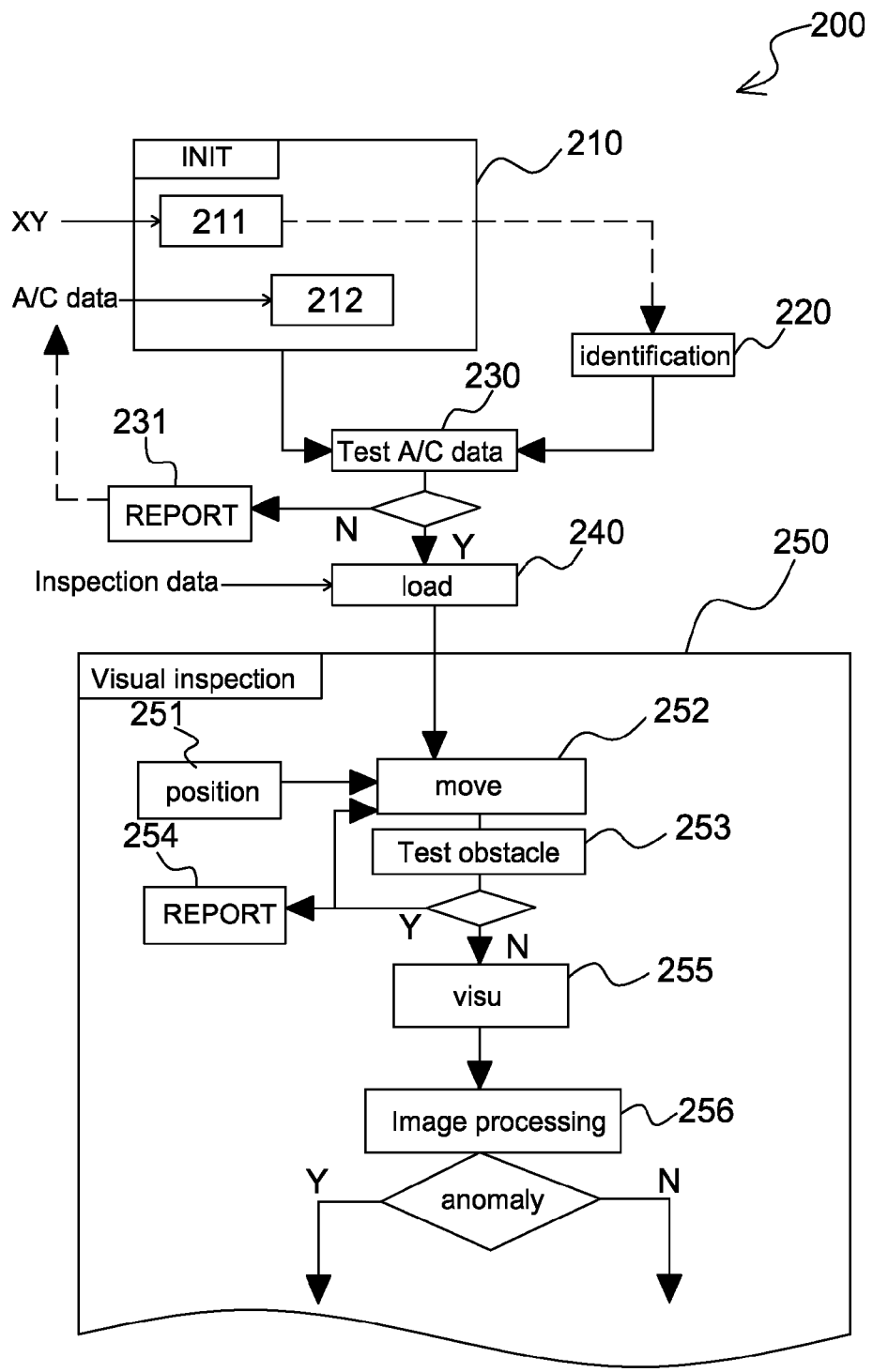
FIGS. 2A-B are example of a flow diagram of the main steps in the visual inspection method using a collaborative robot and a remote control center.
Figure 2B:
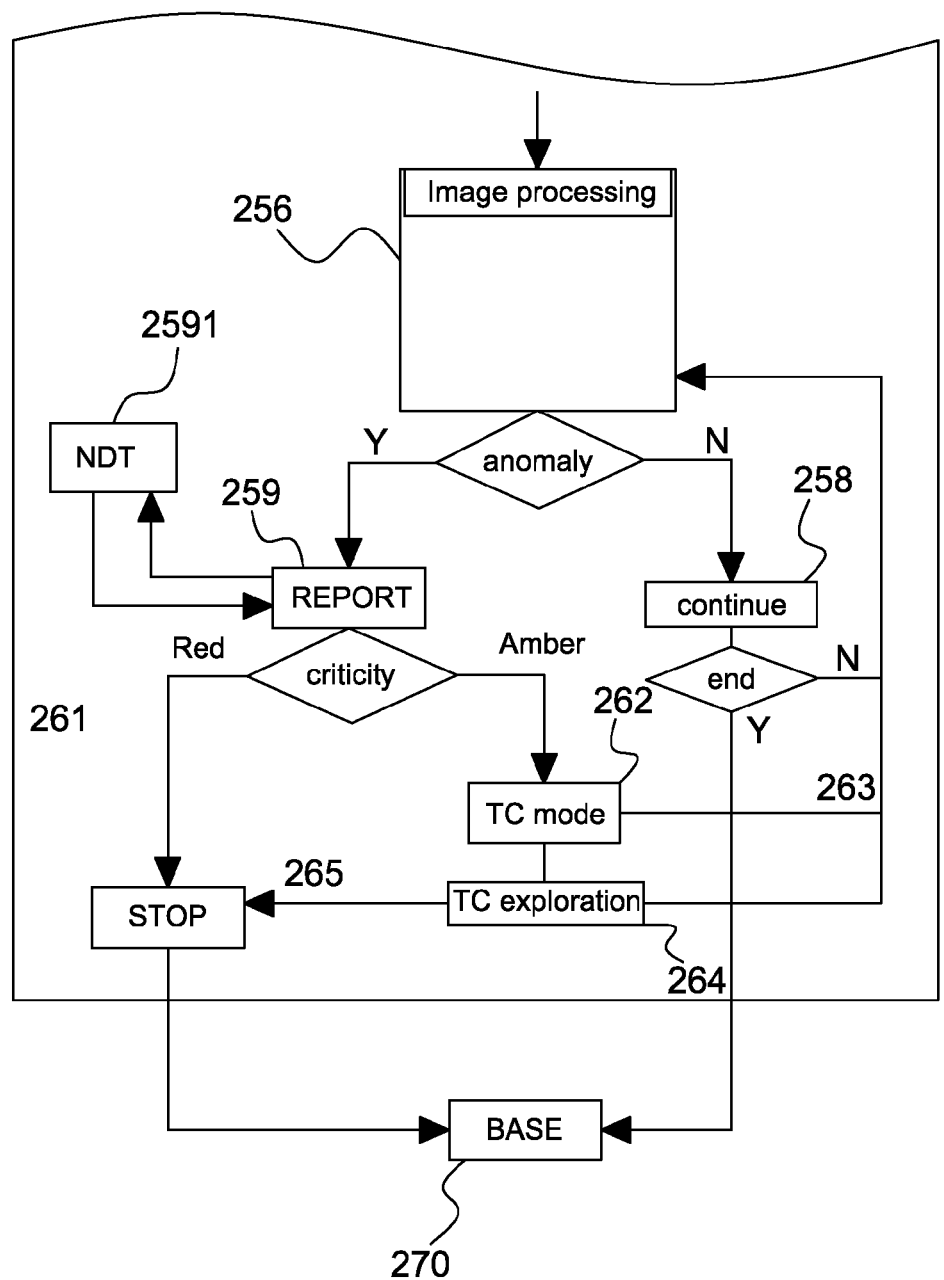

A collaborative robot for inspecting an aircraft 90 such as the robot 10 illustrated in FIG. 1 comprises a mobile platform 11 provided with a turret 12 carrying viewing means 13.

The mobile platform 11 illustrated is mounted on four wheels which give the platform stability and allow it to move along the ground via the motorizing of at least one of the wheels.

Other setups for ensuring the mobility and stability of the platform, for example the use of a greater or lesser number of wheels, for example three wheels or six wheels, or for example caterpillar tracks, which solutions have not been illustrated, are possible. The choice of these means is advantageously made according to the nature of the ground over which the robot 10 will need to move during the inspection operations around the aircraft 90.

The turret 12 is secured in a lower part of said turret to the platform 11, for example to an upper face of said platform, and the viewing means 13, a digital camera in the example illustrated, are secured to the turret 12 in an upper part of said turret.

All of the mechanical connections between the platform 11 and the turret 12, and between the turret 12 and the viewing means 13, are set out in such a way that a main direction of observation 131 of the viewing means 13 can be oriented in elevation and in azimuth in all possible directions in order to aim at points situated above the ground and advantageously also on the ground on which the robot 10 moves, if necessary by taking into consideration the ability of the platform to move, which gives it the possibility to modify the azimuth of a line of sight 111 of said platform.

For example, the turret 12 is built so that the azimuth of the main observation direction 131 can be modified within a limited angular amplitude, for example 180°, the other directions then being achieved by movements of the platform over the ground.

Such an arrangement in particular makes it possible to observe broad zones in terms of azimuth, even without moving the platform.

The capacity for orienting the main observation direction 131 in terms of elevation is advantageously at least 90° between a substantially horizontal aim and an aim substantially vertically upward.

If appropriate, the substantially horizontal aim may be a downward aim so as to allow zones that may be situated under the viewing means 13, which are placed for example in a raised position by means of the turret 12, to be looked down on from above. Such zones are, for example, parts of the ground under the aircraft which may bear traces of leaks of a fluid from the aircraft. Such zones are, for example, treads of tires which are likely to bear traces of abnormal wear or structural parts that can be looked down on from above because of the raised position of the viewing means.

In one embodiment, the turret 12 comprises elevation means 121 for raising the viewing means so as to modify the height of said viewing means above the ground.

Such elevation means 121 consist for example of an assembly of articulated arms, two or more arms, which can be unfolded or folded by actuators, not depicted, so that the height of the upper end of the turret 12 carrying the viewing means 13 above the platform 11, and therefore above the ground, can be modified.

The viewing means 13, in an elementary form, consist of a camera providing images in the domain of visible light and which are intended to be analyzed. The images may be transmitted in analog form so that they can be processed if appropriate after having been converted to digital form, or may be transmitted in digital form.

Advantageously, the viewing means 13 comprise illuminating means 132, for example secured to the turret 12, oriented to illuminate zones that are to be inspected and that are situated in a field of view of said viewing means.

The illuminating means 132 may be offset from the main direction of observation 131 of the viewing means 13 so as to illuminate from greater or shallower angles so that certain defects such as surface indentations can be spotted.

The illuminating means 132 may also be arranged so as to produce illumination in particular domains of the visible light spectrum, in red, green or blue for example, or the non-visible domain of the spectrum, corresponding to specific spectral bands of the infrared or ultraviolet spectra, and can advantageously be switched between the various visible or non-visible spectral bands.

The light spectra of the illumination means 132 are fixed according to the spectral sensitivities of the cameras used by the viewing means 13 and according to the expected behaviors of the inspected zones under the various types of lighting, particularly when contrast or fluorescence effects are potentially expected in order to show and diagnose an anomaly.

In some embodiments, the viewing means 13 comprise special equipment, not depicted in the drawing, such as, for example, stereoscopic cameras and/or other devices to give a three-dimensional perception, for example using stereo-correlation, shearography, laser telemetry, etc. techniques. A three-dimensional perception makes it possible to check the conformity and detect deformations both on curved surfaces and on planar surfaces.

In one preferred embodiment, the mobile platform 11 is autonomous in terms of power supply.

Propulsion may be afforded by combustion engines that drive the wheels in order to move the mobile platform along, for example using a hydrostatic transmission, and to produce hydraulic and/or electrical energy needed for the actuators useful for moving the turret 12 and the viewing means 13.

Propulsion may also be afforded by electric motors powered by electric generator means carried by the platform or by accumulator batteries. The use of accumulator batteries to power electric motors and electric actuators for moving the mobile platform 11 and the turret 12 proves to be well suited to the inspection of aircraft performed in an airport environment that has readily available infrastructures for recharging the accumulator batteries between two inspections or whenever necessary.

The collaborative robot 10 further comprises calculation means 20 needed for the visual inspection.

The calculation means 20 notably comprise data acquisition means 21 for acquiring observation data that are transmitted via the viewing means 13, processing means 22 for processing said observed data, communications means 23 for communicating with a control center 50 which is remote from a zone in which the collaborative robot 10 is called upon to carry out inspections, and location means 24.

The various means 21, 22, 23, 24 of the calculation means 20 carried on board the robot 10 are advantageously means that communicate with one another digitally via a communications bus of said robot.

The observation data acquisition means 21 consist mainly of numerical data storage memories with sufficient capacity to store observation data for the time needed to process them in order to determine whether anomalies have been observed and, if need be, of means of preprocessing the data so that they can be exploited.

Insofar as comparative data may prove necessary to inspecting a given aircraft, for example between two zones of the aircraft, all of the observation data acquired during a given inspection are advantageously stored at least for the duration of the inspection.

In one embodiment, the observation data are kept in a memory, by the robot 10 or at a remote storage center not depicted, so that they can be downloaded later by the robot, with reference to the aircraft on which said observation data were established, so that the comparative processing that involves comparing observation data between two or more inspections can be performed.

The processing means 22 mainly comprise digital processing units, for example processors and/or microcontrollers, random access memories (RAM), storage memories (ROM, flash memories, SDRAM, hard disks, etc.), digital or analog interfaces and communications buses running between the various components of said processing means.

Where necessary, the processing means 22 comprise circuits specializing in the rapid treatment of the signals transmitted by the viewing means, for example circuits for processing signals corresponding to fixed or moving images.

The processing means 22 are configured to carry out instruction sequences that:

- place the robot 10 in a configuration according to operations to be carried out, particularly an initial configuration dependent on the aircraft being visually inspected;
- ensure communications with remote means;
- control resources used for moving the platform 11, particularly controlling the motor or motors propelling the platform and managing the energy resources of the platform;
- drive actuators of the turret 12 and/or of the viewing means 13;
- process observation data;
- perform diagnostics according to the processed operation data;
- precisely locate the robot 10 and a point being observed on an exterior surface of the aircraft 90 undergoing inspection, in a frame of reference connected with the aircraft, if not continuously at least during observations that are to give rise to the determination of an anomaly.

In general, the robot comprises the mechanical and electronic means that will in the opinion of a person skilled in the art be necessary for the implementation described by way of example hereinbelow.

As will be clear from the implementation example described in detail, the collaborative robot 10 of the invention is not an entirely automated inspection means for detecting anomalies on an aircraft 90 but is an assistance means available to an operator for carrying out a visual inspection.

The collaborative robot 10 is in particular suited to allowing the operator to perform an inspection remotely and to providing assistance with inspection for diagnoses that are more accurate, more detailed, more repeatable and more reliable.

According to the visual inspection method 200, in a first step 210, when an aircraft 90 is to be inspected, for example for a pre-flight check, a collaborative robot 10 is initialized so that it is in a state capable of performing the desired inspection.

During this first step 210, the robot 10 receives a position 211 of the aircraft 90 that is to be inspected, at least an approximate position such as the number or geographical position of a post on which the aircraft is placed, and receives information 212 about the aircraft that is to be inspected, at the very least an aircraft type and preferably also the identity of the aircraft.

It should be noted as far as the position of the aircraft is concerned that said position may be implied, for example if the collaborative robot is assigned to a particular post and that if this is the case, so far as the robot is concerned, the aircraft will always be assigned to that same spot.

When, on the other hand, the collaborative robot 10 may need to perform inspections on aircraft that may be parked at different spots in a parking zone, the robot will then be informed, right from the first step 210, as to the location at which to find the aircraft 90 that is to be inspected.

In one embodiment, during a second step 220, the collaborative robot 10, when it has reached the zone in which to find the aircraft 90 that it is to inspect, makes an overall examination of the aircraft using its viewing means 13, and from this examination deduces, from a database containing the shapes of the aircraft, which type of aircraft is involved. For preference, the collaborative robot 10, by processing the images acquired during this step, detects the registration number of the aircraft and, by consulting a database containing the registered aircraft, checks that the type of aircraft bearing said registration does indeed correspond to the type identified by analyzing the shape of the aircraft.

In one embodiment, the information about the aircraft 90 which is obtained during the first step 210 and during the second step 220 is compared during a third step 230 so as to check that the data transmitted by the control center is consistent, so that any inconsistency can be detected as early on as possible.

Any anomaly or inconsistency detected during the third step is immediately reported 231 by the collaborative robot 10 to an operator responsible for the inspection who will then decide what action to take: whether the robot should interrupt the inspection in order to correct the information regarding the type and identity of the aircraft, whether the robot should be sent orders to obtain additional visual data before a decision is taken, whether the collaborative robot is to be given instructions to continue with the inspection disregarding certain detected inconsistencies, if need be by also requesting operator intervention in order to perform an in-situ analysis and get rid of any doubt.

In a fourth step 240, which fourth step may be conducted during the previous steps on the basis of instructions received by the collaborative robot, said collaborative robot 10 downloads the data it needs for the inspection that it is to carry out, at least if it does not already have all said data in its internal storage memories.

Said data for example comprise an inspection circuit to be carried out, which is determined by a nominal path, lists of operations that are to be carried out by way of inspection of the type of aircraft, lists of inspection operations that are to be carried out according to the particular aircraft, for example bearing in mind previous observations on the same aircraft or on other aircraft of the same type.

In one embodiment, said data, at least in the case of some of them, are acquired by the collaborative robot through a learning process, for example during inspections performed in remote-controlled mode, and are supplemented during successive inspections in order to improve the future detection of anomalies that have been detected.

Said data also include the characteristics of the aircraft, nominal geometric characteristics, colors and patterns painted on the airplane, position and types of hatches, latches, probes, etc. that are to be checked during the visual inspection, known anomalies, for example those detected during previous inspections, etc.

In a fifth step 250, the collaborative robot 10 will carry out the visual inspection operations according to the inspection circuit by moving along the ground near the aircraft 90.

As it moves, the collaborative robot 10 will determine 251 its position continuously in a frame of reference connected with the aircraft being inspected, for example an OX-OY frame of reference on the ground the plot of which corresponds to a longitudinal axis X of the aircraft and to a transverse axis Y of the aircraft.

In order to determine its position, the collaborative robot 10 uses conventional techniques, for example the recognition of markers consisting of characteristic shapes or subassemblies of the aircraft, data which are advantageously coupled to geolocation information, for example from GPS, laser telemetry or other location finding devices, and to odometry techniques so as to integrate the movements of said robot, the various techniques advantageously being hybridized in order to make precise estimates of the position and orientation of the robot in the OX-OY frame of reference, which precision is typically of the order of one centimeter or under in terms of position and one minute of angle or under in terms of orientation.

Although the collaborative robot 10 is called upon to operate on a substantially planar and horizontal surface of an aircraft parking area of an airport installation, the location techniques used if appropriate make it possible to determine a relative heightwise position of the robot with respect to the aircraft.

If appropriate, the inclination of the platform with respect to a local vertical is also determined, particularly if said collaborative robot 10 is not provided with a stabilizing function to keep the mobile platform 11 horizontal, or an axis of the turret 12 vertical.

The robot 10, according to the instructions stored in memory in a program of the processing means, will move in a path that allows it to view all of those points of the aircraft that are to be inspected.

The robot 10 overall follows 252 a predetermined path 91 along the ground.

As it moves, the robot detects 253 potential obstacles, for example using optical means and/or using specific sensors, for example by ultrasound emitting sensors, and if necessary diverges from the predetermined path by making the movements necessary to circumnavigate the obstacle or obstacles and ensure that the visual inspection of all the zones to be inspected is performed correctly.

Furthermore, a detected obstacle is signaled 254 to the operator responsible for the inspection as being a potential anomaly that needs to be processed before the aircraft 90 leaves the parking area.

In order to carry out the visual inspection, the robot, according to its position and orientation estimated in the frame of reference OX-OY positions and orients 255 the viewing means so that images of the zones of the aircraft that are to be inspected are captured and transmitted to the processing means 22.

In one embodiment, the images are captured continuously as the robot moves along and during its stoppages so as to view zones of the airplane that can be observed on the ground given the possibilities of orienting the viewing means 13 and elevating them above the ground.

The processing means 22 carry out processing 256 of the images received so as to identify any type of anomaly which is manifested in characteristics that can be identified in the images. For example, such characteristics correspond to geometric singularities and/or contrast and/or colorimetric singularities, which singularities can be seen in one or more lighting spectra, the robot switching between lighting spectra during the positioning and orientation step 255.

In one embodiment, the robot 10 selects a given spectrum for the lighting means 132 according to the type of anomaly being looked for in a zone being inspected or according to the appearance of a detected anomaly, for example in white light, in order to make a diagnosis.

The lighting spectrum is, for example, in the domain of visible light, white light, or in a particular color of the visible spectrum, or in the domain of infrared or ultraviolet, for example to identify zones that have particular fluorescence properties.

Such fluorescence properties may be the direct trace of an anomaly such as, for example, the leak of a liquid, such as fuel, hydraulic fluid or some other fluid, that leaves a visible trace on an exterior surface of the aircraft and/or on the ground. They may for example be a sign of an aircraft that is electrically charged with electrostatic charges, through the presence of corona discharges that can be seen at the fuselage or wing static wicks.

They may also be the result of markers revealed by particular conditions for example following exposure to abnormal heat or to an impact. Such markers consist for example of paint the spectral properties of which become modified through exposure to heat or by paint containing microspheres filled with a fluid that becomes visible when illuminated with light of a particular wavelength and the fluid of which is dispersed at the time of mechanical impact onto a surface covered with such paint.

In the case of visible structural parts, the image processing is performed, not only to make detections using revealers like those mentioned hereinabove but also to detect abnormal shapes or changes in shape between successive inspections, or asymmetries in shape between zones of the airplane that are nominally symmetrical, for example bulging or indentation, such changes in shape generally being interpreted as structural anomalies.

In the case of the particular zones that are to be inspected in order to check their status and integrity, the processing means 22 perform an analysis of the images transmitted by the viewing means 13 by analogy with virtual depictions of the observed zones, particularly of elements situated in these particular zones, which are stored in memory. The virtual depictions are, for example, three-dimensional digital depictions or views that allow a virtual depiction to be placed at the position, orientation and distance at which the actual particular zone is observed by the viewing means 13 so that digital processing can be used to compare the real element with its virtual depiction. In this particular case, anomalies of more or less large dimensions can be looked for according to pre-established criteria, the viewing means 13 advantageously being provided with magnification means, for example of the optical zoom type, in order to look for small-sized defects.

The particular zones are, for example, zones containing a door or an inspection hatch, or engine covers the closure and position of the locking devices of which need to be checked.

The particular zones are, for example, zones containing visible equipment such as an incidence sensor, a total aerodynamic pressure tapping, a static pressure tapping, an icing detector, an antenna, a drain or any other type of element that may become damaged, for example twisted or pulled off or plugged, for example by pitot covers.

During the inspection, the collaborative robot transmits inspection reports to the control center 50 supervised by an operative responsible for inspecting the aircraft.

If the robot 10 does not detect any anomaly 258 in an inspected zone, it transmits information regarding the absence of a detected anomaly, for example this taking the form in the control center of a "green light" and information regarding the progression of the inspection that can be displayed on a screen 51 in the control center 50 in order to be monitored.

If the robot detects an anomaly 259 it forwards an alarm to the control center 50, which alarm is accompanied by images of the visual observation of the zone that has given rise to the detection of the anomaly with a diagnosis or list of possible diagnoses according to their probabilities given the typology of the anomaly processed by the robot 10.

If the collaborative robot 10 identifies an anomaly associated with a high probability that the anomaly will affect safety, said collaborative robot interrupts 261 the inspection and transmits an anomaly detection report to the control center 50 with the alert message and a "red light" (warning) alarm, intervention on the aircraft in this instance being in theory necessary.

If the collaborative robot 10 identifies an anomaly for which said collaborative robot is not capable of making a diagnosis, except with a high degree of uncertainty as to the consequences of the anomaly, said collaborative robot transmits the alert message with an "orange" alarm (caution) and switches to a standby condition and a remote-controlled mode 262 in which it awaits instructions from the operator responsible for the inspection.

The operator may, after studying the images and data transmitted by the collaborative robot, decide:
- to send the robot an order to continue with the visual inspection 263, considering that this is a false alarm or that the detected anomaly is minor;
- or remotely control 264 the robot in order to obtain additional data regarding the zone that has given rise to the alarm and be able to take a decision to continue 263 or stop 265 the visual inspection;
- or have the inspection performed by the robot 10 supplemented by an intervention of an inspection crew on the aircraft 90.

In one particular embodiment, the data gathered by the robot 10 and the diagnostics information supplied by the operator via the control center 50 are processed in order to enrich anomalies databases and ensure during subsequent inspections that the type of anomaly encountered by the robot 10 performing the visual inspection or by a fleet of inspection robots can be better detected.

It must be noted that it is beneficial to the robot 10 to take account of all the specifics of the aircraft 90 that it is inspecting. Indeed it is not uncommon for a given aircraft to have its own peculiarities compared with other aircraft of the same type.

For example, one given aircraft may have an antenna that is absent on other aircraft of the same type or an antenna of a different model, which situation could give rise to a false anomaly detection.

Knowledge by the robot 10 of the precise identity of the aircraft 90 allows it to have available information specific to this aircraft and, for example, information that the aircraft in question has a peculiarity in a certain zone, for example an antenna fixed to this particular aircraft.

Furthermore, if the database of characteristics of the aircraft 90 does not include the presence of an observed peculiarity, the operator responsible for the inspection, alerted by the robot 10 to a detected anomaly, will be able to observe for example that the antenna looks normal and confirm this information to the robot which will enrich the database relating to the aircraft 90 for the next inspections thus avoiding further alerts when detecting the same false anomaly.

When the robot 10 during an inspection is looking for potential anomalies on an aircraft 90, during the fifth step of the method, it successively inspects the various zones of the aircraft in order to detect visible traces attributable to an abnormal state of the aircraft.

In order to do that, the robot 10 moves around the aircraft 90, methodically with the viewing means 13 scanning the various parts of the aircraft, or even the ground underneath the aircraft. The images obtained are, after processing, compared against data representative of normal situations and of abnormal situations in order to detect the presence of any potential anomaly.

For the purposes of this detection, the images obtained by the viewing means are, wherever necessary, processed so that they can be compared against the data in the database known to the robot 10.

The images are also analyzed in order to identify any potential generic characteristics of potential defects such as, for example, deformations at the exterior surface of the aircraft 90, missing parts which in practice manifest themselves as uneven openings or openings at locations at which the robot does not recognize that an opening ought to be present, traces such as scratching or runs on the exterior surface of the aircraft, absences of paint at certain points, traces showing the appearance of a lightning strike, etc.

The defects potentially associated with these characteristics are not in practice looked for at particular points but may be discovered at numerous points on the exterior surface of the aircraft.

The processing performed on the images may be general or specific to the detection of a particular problem. For example, the images are processed using contrast enhancement algorithms, algorithms for extracting zones from the image according to their color or spectral sensitivity, for extracting contour, texture, etc.

The detection may for example relate to a shape or a color which does not conform to the nominal shape or color, it being possible for the shape or color observed to be a deformation or the presence of a foreign body.

A shape anomaly manifests itself as an observed shape that does not correspond to the expected shape.

When an anomaly is detected, the robot 10 characterizes the anomaly on the one hand by its type, namely the characteristics that led to the conclusion that an anomaly might be present, for example the shape, the color, the extent, the sensitivity to certain wavelengths, the presence or absence of an unexpected or expected element, the contrast, etc. and on the other hand quantifies the anomaly.

The robot also locates the observed anomaly in the axis system of the aircraft, which location it performs taking into consideration its own precise position in the Ox-Oy axis system in which it moves around on the ground, the direction in which the viewing means are oriented and the geometric characteristics of the aircraft being observed.

Knowledge of the position of the anomaly from the exterior surface of the aircraft is advantageously used by the processing means 22 to carry out a diagnosis on the anomaly. For example, it is known that lightning has its own preferred points on an aircraft to strike and the presence of a trace showing the appearance of a lightning strike will not necessarily be interpreted in the same way as regards its causes and effects depending on the location at which said trace is found.

Returning to the example of a lightning strike, knowledge of the position of the anomaly on the surface of the aircraft also makes it possible to attribute the anomaly to structural characteristics of the aircraft at the location of the anomaly. For example, the structure may be a metallic structure or a structure made of composite material with properties dependent on the type of composite material, and in the latter instance with protection against lightning currents which may differ, for example bronze mesh of greater or lesser density or particular conducting paint.

From the knowledge by the robot 10 of the physical and dimensional characteristics of the surface of the aircraft 90 at which an anomaly of a particular type is identified, and of the characteristics of the non-visible structure beneath the visible surface, for example the presence of a stringer or of a structural frame, an equipment support or an item of equipment, the processing means make a prognosis so as to be able to provide the operator in charge of the inspection with detailed information regarding the anomaly and the attendant risks.

Detection of an anomaly of the impact type from the exterior surface of the aircraft during the inspection results for example in a message sent to the control center of the "indentation in fuselage covering at No 14 stringer between fuselage frames 11 and 12—no traces of tearing of covering—low structural risk, repair to be scheduled" type, accompanied by images of the zone concerned.

In a preferred form, the processing means perform a quantitative analysis of the defect: extent (surface area, length, width, etc.) of the anomaly, for example of an area affected by an impact, depth of a deformation, intensity of a cause that has led to the observed anomaly, such as a rise in temperature, intensity of a leak in the case of the presence of a suspect fluid, etc.

In order to perform this quantitative analysis, the robot 10 wherever possible uses its visual means associated with the processing means as already specified by stereoscopic vision techniques or any other known optical method such as shearography, holography, telemetry, etc.

In one embodiment, the robot 10 conducts examinations of the structure using non-destructive testing equipment in order to quantify the anomalies.

When in step 259 an anomaly is detected by visual inspection, the robot, depending on the diagnosis performed, positions itself, in step 2591, with respect to the anomaly so as to deploy the non-destructive testing instruments, not depicted, so as to obtain additional information in order to improve the diagnosis based on the visual inspection.

Such non-destructive testing means may employ probes, for example ultrasound probes, eddy current probes, temperature measurement means such as thermal cameras or any other type of probe capable of conducting a local examination of the material in a particular zone.

Advantageously, the probes are carried by one or more articulated arms so that the robot can apply/orient said probes against/toward the locations that are to be examined, each probe, during an examination using said probe, being associated with measurement equipment carried on board the platform of said robot.

In one embodiment, in which the robot comprises a plurality of probes, the probes are wrapped in a probe support of the robot so that they can be used via one and the same articulated arm.

In order to conduct the non-destructive examination, the articulated arm, driven by the processing means of the robot or by an operator from the control center 50 who has chosen to control the examination remotely, picks up the desired probe for a given examination, using any type of gripper means and means of connection to the measurement instrument to which the probe is to be connected, then applies/orients the probe against/toward the zone that is to be tested by performing the desired movements of said probe and, when the test has been performed and the processing means and/or the remote operator consider that all the data necessary for the inspection have been obtained, the articulated arm places the probe back in the probe support.

Depending on the results of the examination transmitted to the control center 50, if appropriate with a diagnosis performed by the processing means 22, and subject to instructions received from said control center, the robot 10 continues with the inspection.

When the inspection of the aircraft or the part of the aircraft assigned to the robot 10 is over, said robot returns to a standby station 30 in a sixth step 270, advantageously a standby station that affords said robot some protection to prevent it from being damaged by the various vehicles and aircraft moving around on the airport platform, and preferably a position in which said robot connects to a power source that allows it for example to recharge its electric accumulator batteries if it is provided with same.

In one embodiment, the standby station 30 is provided with short-range communication means 31 for communicating with the robot, if appropriate wired connections, to allow rapid exchanges of information with low risk of interference between the control center 50, for example so that all the data collected during the inspection can be transmitted so that said data can be stored and a delayed processing potentially be carried out.

Such means may also be used in the first step 210 when the robot 10 is loading the information it will need for its upcoming inspection.

In one embodiment and implementation, the data transmitted by the robot 10 to the control center 50 during the visual inspection may be received by control station equipment so that a member of the technical team has the option of monitoring the progress of the inspection and of assessing any anomalies detected.

In an alternative form of this embodiment, control means of the robot are arranged in the control station so that the inspection can be influenced from there.

Advantageously, despite the possibility of remote intervention on the robot during the visual inspection, the robot resumes the inspection so that all the requirements nominally laid down for an inspection are met before the inspection can be declared to be complete.

In that case, a "light" showing the status of the inspection remains "red" as long as all the requirements have not been met, if appropriate turning "orange" if only requirements deemed to be ancillary requirements by the operative responsible for the inspection have not been performed.

As it moves around, both during the inspection and when making its way to the inspection site and when leaving said site, the robot 10 ensures safety in order to avoid collision with people or objects fixed or animate that may find themselves in its close environment. For example, the robot 10 uses its viewing means 13 to detect the objects with which it could collide. The robot may also comprise means specifically dedicated to the detection of such objects.

When the processing means 22 identify or are alerted to a risk of collision, said means command the movements of the platform to avoid the collision, if appropriate by emitting an acoustic signal and/or light signal or some other signal in order to alert an individual who may become involved in the potential collision.

Advantageously, the processing means guide the platform autonomously to avoid the risk of collision by using the known techniques of location with respect to an environment of which they reconstruct the characteristics, for example by using an SLAM (Simultaneous Localization and Map Building) method.

According to the implementation embodiment just described, one single robot 10 performs the visual inspection of the airplane 90.

In another implementation of the visual inspection method, the robot performs partial visual inspections in combination with partial inspections performed by other similar or specialized robots.

For example, several robots may be used, which solution has not been illustrated, to inspect various parts of the aircraft so that a full inspection can be performed in a shorter space of time.

In that case, use is made for example of two or more identical robots to perform the visual inspection of the right-hand side of the aircraft and of the left-hand side of the aircraft, and/or of the front part and of the rear part.

In this case, the inspections performed by two robots are, for example, synchronized so as, for example, to obtain comparative data between two zones of the aircraft such as a zone on the right-hand side and a zone theoretically symmetrical on the left-hand side so as to identify or confirm the presence of an anomaly.

Use may also be made of robots with different capabilities, for example suited to parts of the airplane for which it is necessary to employ particular viewing means, for example because of their heights, such as a tail of an airplane, or because of their shapes, such as engine air intakes or engine jet pipes.

In one particular embodiment using non-destructive testing means, all or some of the non-destructive testing means are carried by at least one test robot the mobile platform of which is independent of the visual inspection robot 10.

In that case, the test robot is controlled by the visual inspection robot 10 which, when it has identified a zone that needs to undergo a non-destructive testing, sends an intervention order to the test robot with all of the data that said test robot will need in order to perform the requested test, particularly the precise location on the aircraft of the zone that is to be tested and the extent thereof and the type of test desired. When the test robot has completed the requested test it transmits to the visual inspection robot the data obtained from the test, possibly processed in order to provide an interpretation of the test, and said test robot goes into standby.

The use of a separate test robot entails the creation of a specific mobile platform for this test robot but does allow the visual inspection robot to be simplified, its cost decreased and its agility increased.

Furthermore, one and the same test robot, which is called upon to act only occasionally and at the request of a visual inspection robot, can serve several visual inspection robots, priority rules governing potential conflicts if two visual inspection robots call upon the test robot at the same time.

In one embodiment, different types of test robot are used, for example one robot for performing ultrasonic testing and another robot for performing eddy current testing. This form of embodiment yields test robots that are more or less specialized and the performances of which can be adapted to suit each of the types of test.

The example of a visual inspection robot 10 described in the embodiment is a robot that moves along the ground, although other types of robot, for example hovering robots, may be used, possibly combined with one or more robots on the ground.

In one embodiment of the robot 10, said robot comprises means, for example carried by an articulated arm, for opening and closing doors at the surface of the airplane that give access from outside of the airplane 90 to intakes or indicators so that the robot 10 is capable of closing a door that has been left open inadvertently or of opening a door in order to make a visual inspection of a housing and then close said door to the housing afterwards.

It is thus possible to carry out, with a visual inspection robot 10 or with a low number of inspection robots, a visual inspection of an aircraft, for example an airplane, in a non-specific environment, for example on a parking place of an airport.

The inspection is carried out as a collaboration between the robot 10 and the remote operator responsible for the inspection, to whom said robot returns all of the results of the visual inspection, if appropriate results of non-destructive tests of a zone exhibiting a visually detected anomaly, and from whom it awaits instructions each time an anomaly is detected and a decision requires the intervention of the operator to whom the images and all the features of the anomaly that could be measured are presented.

According to the visual inspection device and method, the operator responsible for the visual inspection retains complete control over the decision to declare the absence of an anomaly affecting the operational use of the inspected aircraft with the possibility of intervening remotely on the robot in order to obtain all the information, particularly the images of dubious zones, that enable him to make a rapid decision suited to the individual circumstance.

The control center from which the operative responsible for the inspection works may be remote from the visual inspection site, for example a visual inspection operative may be situated in a maintenance center of the aircraft operator and supervise visual inspections at airports worldwide particularly using digital links that can be had over landlines, terrestrial radio networks and satellite radio networks.

The invention claimed is:

1. A visual inspection device to visually inspect exterior surfaces of an aircraft parked in an inspection area, comprising
    a visual inspection robot comprising a mobile platform carrying a turret with a camera and a processor to guide the mobile platform and process information received from the camera;
    a control center with a station for at least one control operator; and
    wherein the processor of the visual inspection robot:
        drives the visual inspection robot autonomously during a visual inspection of the exterior surfaces of the aircraft parked in the inspection area;
        detects an anomaly on the exterior surfaces of the aircraft during an on-going visual inspection;
        interrupts the on-going visual inspection;
        determines a position of the detected anomaly with respect to elements of an internal structure of the aircraft which are not visible from outside of the aircraft;
        process data of the detected anomaly as a function of the position to perform a diagnosis of the detected anomaly;
        transmits the diagnosis and visual inspection information of the detected anomaly that interrupted the visual inspection to the control center; and
        waits for instructions from the control center as to an action to perform after the visual inspection interruption.

2. The visual inspection device as claimed in claim 1, wherein the visual inspection robot comprises a position detector to determine at any time during the course of the visual inspection a position of the visual inspection robot and an orientation of the camera in an axis system connected with the aircraft.

3. The visual inspection device as claimed in claim 2, wherein the processor of the visual inspection robot determines the position of the visual inspection robot and the orientation of the camera by processing images of the aircraft being inspected and that are obtained by the camera.

4. The visual inspection device as claimed in claim 2, in which the visual inspection robot comprises an absolute-location device, the absolute-location device is at least one of the following: a GPS receiver, optometry or laser telemeters aimed at reference targets and a movement integration device.

5. The visual inspection device as claimed in claim 1, wherein the processor comprises a data storage unit to store data at least temporarily comprising at least one of geometric and graphic characteristics of the aircraft being inspected.

6. The visual inspection device as claimed in claim 1, wherein the processor comprises a data storage unit to store data comprising anomaly characteristics to provide an anomalies library.

7. The visual inspection device as claimed in claim 1, wherein the processor comprises an image processor to detect, in images transmitted by the camera, anomalies visible to the viewing unit in a wavelength belonging to an optical spectrum.

8. The visual inspection device as claimed in claim 1, wherein the camera comprises an illuminating element configured to illuminate a light from a visible domain, from an infrared domain or from an ultraviolet domain.

9. The visual inspection device as claimed in claim 1, wherein the camera and the processor determine a three-dimensional shape of inspected exterior surfaces of the aircraft.

10. The visual inspection device as claimed in claim 1, further comprising a testing device to perform a non-destructive testing of a structure of the aircraft.

11. The visual inspection device as claimed in claim 10, wherein the visual inspection robot performs all or some of the non-destructive testing.

12. The visual inspection device as claimed in claim 10, wherein all or some of the non-destructive testing is performed by at least one control robot controlled by the visual inspection robot.

13. The visual inspection device as claimed in claim 1, wherein the camera is orientable in an elevation and in an azimuth with respect to a frame of reference of the mobile platform of the visual inspection robot.

14. The visual inspection device as claimed in claim 1, wherein the visual inspection robot is configured to travel by rolling over the ground of the inspection area or by hovering in a volume a footprint of which corresponds substantially to the inspection area.

15. The visual inspection device as claimed in claim 1, further comprising a plurality of inspection robots configured to jointly perform the visual inspection of one and same aircraft.

16. A visual inspection method for a visual inspection of an aircraft with the visual inspection device according to claim 1, comprising steps of:

transmitting images of an exterior surface of the aircraft being inspected to the processor of the visual inspection robot;

analyzing the images by the processor to identify a presence of any potential visible anomalies; and wherein, in response to the detection of an anomaly, the processor of the visual inspection robot:
  interrupts the on-going visual inspection of the visual inspection robot;
  determines the position of the detected anomaly with respect to the elements of the internal structure of the aircraft which are not visible from outside of the aircraft;
  process data of the detected anomaly as a function of the position to perform a diagnosis of the detected anomaly;
  transmits the diagnosis and data relating to the detected anomaly that interrupted the visual inspection to the control center; and
  waits for instructions from the control center as to an action to perform after the visual inspection interruption.

17. The visual inspection method as claimed in claim 16, in response to an interruption of the visual inspection due to the detected anomaly, instructions are transmitted to the visual inspection robots by the control center to continue with the visual inspection, the visual inspection robot continues with the visual instruction in accordance with the instructions.

18. The visual inspection method as claimed in claim 16, further comprising the step of calculating an amplitude of the visible anomaly by the processor using at least one of an optical sensor to measure deformations and colorimetric analysis in at least one of a visible, infrared and ultraviolet domain of a light spectrum.

19. The visual inspection method as claimed in claim 16, in response to the detection of the visible anomaly, a zone affected by the visible anomaly is subjected to a non-destructive testing by the visual inspection robot or a non-destructive testing robot controlled by the visual inspection robot.

20. The visual inspection method as claimed in claim 16, further comprising a step of performing an analysis of images transmitted by the camera of particular zones in the exterior surfaces of the aircraft by comparison with stored virtual depictions corresponding to said particular zones.

21. The visual inspection method as claimed in claim 16, wherein the processor performs and transmits to the control center the diagnosis or a list of possible diagnosis as a function of their probability given a typology of the anomaly processed.

22. The visual inspection device according to claim 1, wherein the camera and the processor identify at least one of contrast and color singularities on at least one of the exterior surfaces of the aircraft and on ground zones underneath the aircraft.

* * * * *